United States Patent
Mardirossian

[11] Patent Number: 6,011,991
[45] Date of Patent: Jan. 4, 2000

[54] COMMUNICATION SYSTEM AND METHOD INCLUDING BRAIN WAVE ANALYSIS AND/ OR USE OF BRAIN ACTIVITY

[75] Inventor: Aris Mardirossian, Germantown, Md.

[73] Assignee: Technology Patents, LLC, Derwood, Md.

[21] Appl. No.: 09/206,365

[22] Filed: Dec. 7, 1998

[51] Int. Cl.[7] .................................................. A61N 5/00
[52] U.S. Cl. ............................................ 600/544; 600/545
[58] Field of Search ............................ 600/300, 544–545; 128/897–898, 904, 905

[56] References Cited

U.S. PATENT DOCUMENTS

| | | |
|---|---|---|
| 5,059,814 | 10/1991 | Mead et al. . |
| 5,118,606 | 6/1992 | Lynch et al. . |
| 5,136,687 | 8/1992 | Edelman et al. . |
| 5,224,203 | 6/1993 | Skeirik . |
| 5,303,705 | 4/1994 | Nenov . |
| 5,325,862 | 7/1994 | Lewis et al. . |
| 5,461,699 | 10/1995 | Arbabi et al. . |
| 5,522,863 | 6/1996 | Spano et al. . |
| 5,640,493 | 6/1997 | Skeirik . |
| 5,715,821 | 2/1998 | Faupel . |
| 5,719,561 | 2/1998 | Gonzales . |
| 5,722,418 | 3/1998 | Bro .......................................... 128/905 |
| 5,730,146 | 3/1998 | Itil et al. ................................. 600/544 |
| 5,736,543 | 4/1998 | Rogers et al. . |
| 5,737,485 | 4/1998 | Flanagan et al. . |
| 5,747,492 | 5/1998 | Lynch et al. . |
| 5,791,342 | 8/1998 | Woodard ................................ 600/544 |
| 5,816,247 | 10/1998 | Maynard . |

*Primary Examiner*—Cary O'Connor
*Assistant Examiner*—Michael Astorino
*Attorney, Agent, or Firm*—Joseph A. Rhoa

[57] ABSTRACT

A system and method for enabling human beings to communicate by way of their monitored brain activity. The brain activity of an individual is monitored and transmitted to a remote location (e.g. by satellite). At the remote location, the monitored brain activity is compared with pre-recorded normalized brain activity curves, waveforms, or patterns to determine if a match or substantial match is found. If such a match is found, then the computer at the remote location determines that the individual was attempting to communicate the word, phrase, or thought corresponding to the matched stored normalized signal.

8 Claims, 3 Drawing Sheets

JOE (NO)

JOE (YES)

6,011,991

COMMUNICATION SYSTEM AND METHOD INCLUDING BRAIN WAVE ANALYSIS AND/OR USE OF BRAIN ACTIVITY

This invention relates to a system and method for enabling human beings to communicate with one another by monitoring brain activity. In particular, this invention relates to such a system and method where brain activity of a particular individual is monitored and transmitted in a wireless manner (e.g. via satellite) from the location of the individual to a remote location so that the brain activity can be computer analyzed at the remote location thereby enabling the computer and/or individuals at the remote location to determine what the monitored individual was thinking or wishing to communicate.

In certain embodiments this invention relates to the analysis of brain waves or brain activity, and/or to the remote firing of select brain nodes in order to produce a predetermined effect on an individual.

BACKGROUND OF THE INVENTION

It is known to monitor brain activity by way of electroencephalograph (EEG) methods, magnetoencephalograph (MEG) methods, and the like. For example, see U.S. Pat. Nos. 5,816,247 and 5,325,862, the disclosures of which are both hereby incorporated herein by reference. As discussed in the '247 patent, an EEG may be recorded from a number of pairs of scalp electrodes and processed according to known software. Such software and/or hardware acquires both processed and unprocessed EEG data and may record it on a disk. The records may be replayed and statistics of the on-line measures made on suitable sections placed in categories predefined by a user. This may utilize the form of database of statistical measures of brain activity. Unfortunately, neither the '862 nor the '247 patents disclose or suggest any methods by which humans can communicate with one another by way of monitoring brain activity.

U.S. Pat. No. 5,719,561 discloses a communications device and method, the entire disclosure of the '561 patent hereby being incorporated herein by reference. The '561 patent discusses a method and device for vibromechanical tactile communications adaptable for use by individuals to recognize alpha numeric messages in a language or in other symbols known to them. The '561 patent discusses using a series of sequentially firing vibromechanical stimulators vibrating against a suitably tactile sensitive surface of the wearer (e.g. skin) to induce a phenomenon of illustration of linear continuity. Unfortunately, the '561 patent requires the use of burdensome and complex vibromechanical tactile devices, and is not suitable for long distance communication.

It is a purpose of this invention to address any or all of the above-identified problems in the prior art, as well as other problems which will become apparent to the skilled artisan from the following detailed description of this invention.

SUMMARY OF THE INVENTION

Generally speaking, this invention fulfills the above described needs in the art by providing a method of communicating comprising the steps of:

providing a first human being at a first location;
providing a computer at a second location that is remote from the first location;
providing a satellite;
providing at least one sensor (preferably a plurality—e.g. tens, hundreds, or thousands, with each sensor monitoring the firing of one or more brain nodes or synapse type members) on the first human being;
detecting brain activity of the first human being using the at least one sensor, and transmitting the detected brain activity to the satellite as a signal including brain activity information;
the satellite sending a signal including the brain activity information to the second location;
a receiver at the second location receiving the signal from the satellite and forwarding the brain activity information in the signal to the computer;
comparing the received brain activity information of the first human being with normalized or averaged brain activity information relating to the first human being from memory; and
determining whether the first human being was attempting to communicate particular words, phrases or thoughts, based upon the comparing of the received brain activity information to the information from memory.

In certain embodiments, the invention includes the following step: asking the first human being a plurality of questions and recording brain activity of the first human being responsive to the plurality of questions in the process of developing said normalized or averaged brain activity information relating to the first human being stored in the memory. A database in a memory may include, for each of a plurality (e.g. one hundred or thousands) of individuals, a number of prerecorded files each corresponding to a particular thought, attempt to communicate a word, attempt to communicate a phrase or thought, or mental state. Measured brain activity of a given individual may be compared to files from that database of that individual to determine what the individual is attempting to communicate or what type of mental state the individual is in.

In certain embodiments, the plurality of questions are the same question.

In certain embodiments, the plurality of questions are different questions.

In certain embodiments, the invention includes the step of normalizing or averaging recorded brain activity responsive to a given question or set of questions in developing the normalized or averaged brain activity information relating to the first human being.

It is an object of this invention to enable brain activity of a first human being to be monitored, with the activity being transmitted to a remote location so that individuals and/or a computer at the remote location can determine what the first human being was thinking or intending to communicate. In such a manner, human beings can communicate with one another via monitoring of brain activity, and transmission of the same.

It is another object of this invention to communicate monitored brain activity from one location to another in a wireless manner, such as by IR, RF, or satellite.

It is another object of this invention to provide a system capable of identifying particular nodes in an individual's brain, the firings of which affect characteristics such as appetite, hunger, thirst, communication skills (e.g. which nodes are utilized to communicate certain words such as "yes", "no", or phrases such as "I don't know", "I'm not sure", or numbers such as "one", "two", "ten", "one hundred" and the like), thought processes, depression, and the like). When such nodes are identified, they may be specifically monitored by one or more sensors to analyze behavior or communication or words, phrases, or thoughts. In other embodiments, devices mounted to the person (e.g. underneath the scalp) may be energized in a predetermined manner or sequence to remotely cause particular identified brain node(s) to be fired in order to cause a predetermined feeling or reaction in the individual, such as lack of hunger, lack or depression, lack or thirst, lack of aggression, lack of alzheimer's disease effects, or the like.

Brain node firings are the basis of thought and mind processes of individuals. Certain embodiments of this invention enable such brain firings and behavior to be captured by an external device. It is an object of this invention to utilize a normalization or normalizing curve (or waveform or pattern) based upon monitored brain activity to detect or determine thought processes by the monitored individual. In such a manner, individuals can transmit by satellite what they are thinking or intending to think via their monitored brain activity, without the need to talk or write down information.

Each individual has a distinct pattern of brain node firings or brain activity. Each person is believed to be different in this regard. Thus, a separate brain activity file may be stored in a memory for each individual, and analyzed or compared to received brain activity from the monitored individual in order to determine what that individual is thinking or attempting to communicate.

It is an object of this invention to utilize brain monitoring and transmission of monitored brain activity for lie detection and/or human communication.

It is another object of this invention to formulate or build-up a file for each individual based upon patterns recorded in response to that individual answering or responding to numerous predetermined questions with known intended responses. Subsequently, monitored brain activity from that individual may then be compared to information stored corresponding to that individual to determine whether the individual is lying or what the individual is intending to communicate in the monitored brain activity. The higher the level of detail of the file, the higher the level of potential communication by certain embodiments of this invention.

At least one sensor on the scalp or skin in certain embodiments provides signals representative of physiological activity generated in the brain of a monitored individual. A data acquisition device receives the signals representative of the physiological activity generated in the monitored brain, and transforms the signals into a pattern or curve corresponding to the monitored brain activity. This is then transmitted (e.g. by satellite) to a computer located at a remote location, with the monitored brain activity pattern or curve being stored in a memory at the remote location. The computer then causes the received pattern or curve information to be compared with stored brain activity pattern information relating to the monitored individual in order to determine (a) whether the monitored individual is lying in response to a particular question, or (b) what the monitored individual is communicating or attempting to communicate.

Another object of this invention is to utilize normalization curves representative of received brain activity patterns from the monitored individual, and to compare the received normalized data with normalized brain activity pattern or curve data stored in memory relating to that individual. The use of normalization curves in one or both of the individual's file and received brain activity improves reliability, accuracy, and efficiency.

In certain embodiments of this invention, the computer located at the remote location includes a neural network suitably programmed in accordance with known neural network techniques, for the purpose of receiving the monitored brain activity signals, transforming the signals into useful forms, training and testing the neural network to distinguish particular forms and patterns of physiological activity generated in the brain of the monitored individual, and/or comparing the received monitored brain activity information with stored information relating to that individual in order to determine what the individual is attempting to communicate.

This invention further fulfills the above described needs in the art by providing a method of affecting a mental or physiological state of an individual, the method comprising the steps of:

providing at least one firing device capable of being energized on an individual; and energizing the firing device to cause the firing device to cause a particular or group of brain nodes to be fired in the individual in order to affect the mental or physiological state of the individual.

In certain embodiments, the method including the step of providing the at least one firing device on or under the scalp of the individual in proximity of the brain of the individual.

In certain embodiments, the method including the step of identifying at least one brain node related to the mental or physiological state intended to be affected, targeting the identified brain node, and energizing the firing device or devices to cause the identified node to be fired in order to affect the mental or physiological state of the individual.

In certain embodiments, the method is utilized to cause the individual to be one of less hungry, less thirsty, less anxious, and less depressed.

In certain embodiments, the remote node firing devices are electrically energized and generate electromagnetic waves which cause a plurality of brain nodes to be fired.

This invention will now be described with respect to certain embodiments thereof, along with reference to the accompanying illustrations.

IN THE DRAWINGS

Figure 3A:
Figure 3B:
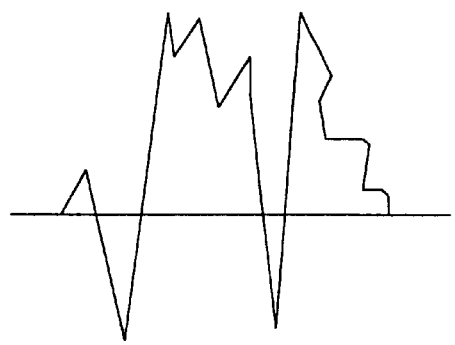
Figure 3C:
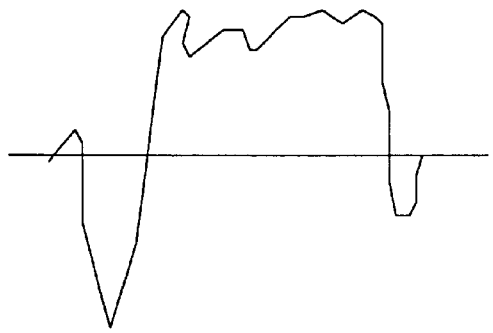
Figure 3D:
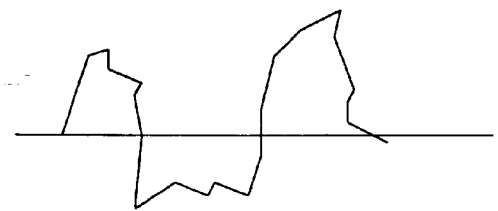
Figure 3E:
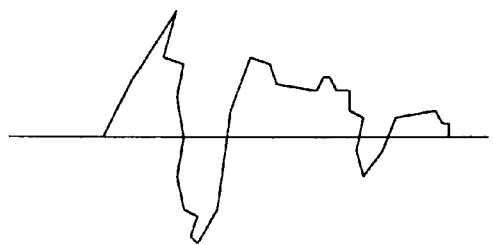
Figure 3F:
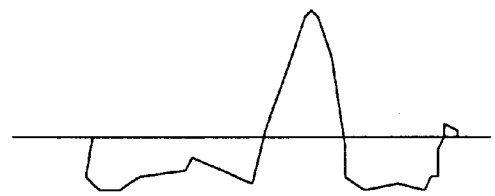

FIGS. 3(a)–3(f) are exemplary graphs of monitored brain activity of different individuals, with, for example, FIG. 3(a) illustrating monitored brain activity of a particular individual who is attempting to communicate the word "no" and FIG. 3(b) illustrating monitored brain activity of the same individual when that individual is attempting to communicate the word "yes."

DETAILED DESCRIPTION OF CERTAIN EMBODIMENTS OF THIS INVENTION

Referring now more particularly to the accompanying drawings in which like reference numerals indicate like parts throughout the several views.

There are significant individual differences in electrical and magnetic activity in the brain. Brain node or synapse firings are chemically and/or electrically caused and/or related. Some characteristics of brain activity may be relatively stable when measured from day to day. Brain responses to sensory stimulation (e.g. visual, audible, olfactory, gustatory, etc.) as well as higher order cognitive processing (e.g. decision-making or thought/word communication), can be examined in great detail using a variety of recording procedures. A recording of brain electrical activity is called an electroencephalograph (EEG), and a comparable record of magnetic activity is called a magnetoencephalogram (MEG). When human sensory systems are stimulated by a particular event (a given sound or optical effect) or when a human wishes to communicate a particular word or phrase (e.g. the word "yes" or the word "no"), there is a predictable sequence of processing that occurs in the brain. This processing generates an event related potential that can be recorded from the scalp beginning shortly after the onset of the stimulation, and lasting for approximately 0.5–4 seconds after the stimulation. These potentials can be repeatedly generated from individuals given the same stimulus or wishing to communicate the same word or phrase. In certain embodiments of this invention, brain activity may be repeatedly sampled, and response patterns averaged by way of a normalization curve or the like. Comparable recordings of averaged or normalized magnetic activity may be referred to as evoked fields. Neuroelectric and neuormagnetic recordings are subsets of general measurings referred to as bioelectric and biomagnetic measures. These measures refer to recordings which may be made from different types of tissue including neural, muscle, heart, etc. For example, EEG, evoked potentials (EP), MEG, position emission tomography (PET) of glucose, or single photon emission computed tomography (SPECT) may be used to monitor brain activity in different embodiments of this invention.

Event related potentials have been shown to be stable and unique to individuals. See U.S. Pat. No. 5,325,862, which is incorporated herein by reference. Although the actual shape of such potentials varies considerably from individual to individual, there is stability within individuals over time for individual waveforms. Sources of these potentials and variations thereof include individual differences in brain anatomy and differences in the way in which information is processed by each individual. Thus, it is feasible herein to utilize monitored brain waveforms for the purpose of determining whether an individual is lying or not, or what word or phrase a particular individual is attempting to communicate (without the need for writing information down or speaking).

Thus, evoked fields and/or event related potentials can be utilized as classifiers for several purposes. For example, because these potentials and/or fields are relatively unique to individuals, an individual's evoked field or event related potential (or brainprint) can be utilized to determine what thoughts an individual is communicating or attempting to communicate given knowledge of the identification of that individual and previously recorded patterns associated with that individual communicating predetermined words, phrases or thoughts. Because there is a remarkable degree of stability in individual waveforms of a person over time, it is possible to identify changes in individual event related potentials and evoked field patterns which can be utilized to determine when an individual is lying, or impaired in any way.

There are numerous neural networks in the brain, these networks having complex inner connections and non-linear response patterns. Relationships between the latencies and amplitudes of event related potentials and evoked field waveform features have become well understood. In addition, there are many individual variations in waveform morphology. Computing techniques modeled after brain neural functions are known in the art. They are typically referred to as neural network analysis techniques or computers. Neural network analysis computing technology offers a method for finding complex, non-linear relationships in large data sets, even when the nature of the relationships is not known in advance. Neural network technology is implemented sometimes using computer software programs, but may also be hardware implemented. Neural network theory, and detailed descriptions of specific techniques, are available in numerous books and articles set forth in the aforesaid '862 patent, as well as in, for example, any of U.S. Pat. Nos. 5,136,687; 5,059,814; 5,461,699; 5,737,485; 5,224,203; and 5,640,493, the entire disclosures of which are all hereby incorporated herein by reference. Such neural computing systems have a capability to learn features of data sets and classify same into either unknown or predetermined categories. A variety of neural network techniques may be utilized to classify event related potentials, evoke fields, or any other type of pattern corresponding to monitored brain behavior. In most neural networks, input values are adjusted through a series of layers by a series of transforms and weighted so that output categories are correctly predicted. Thus, a neural computing system herein may be utilized to receive monitored brain activity and based upon predetermined stored and/or learned information, determine based upon the received information what word, phrase, or thoughts the monitored individual is attempting to communicate. In such a manner, the monitoring of brain activity may be utilized to allow individuals to communicate from one location to another, with the neural computer or any other type of computer analyzing the monitored brain information (e.g. via comparison with previously recorded brain activity of that person) and outputting information indicative of the word, phrase, or thoughts which the monitored individual is attempting to communicate.

Figure 1:
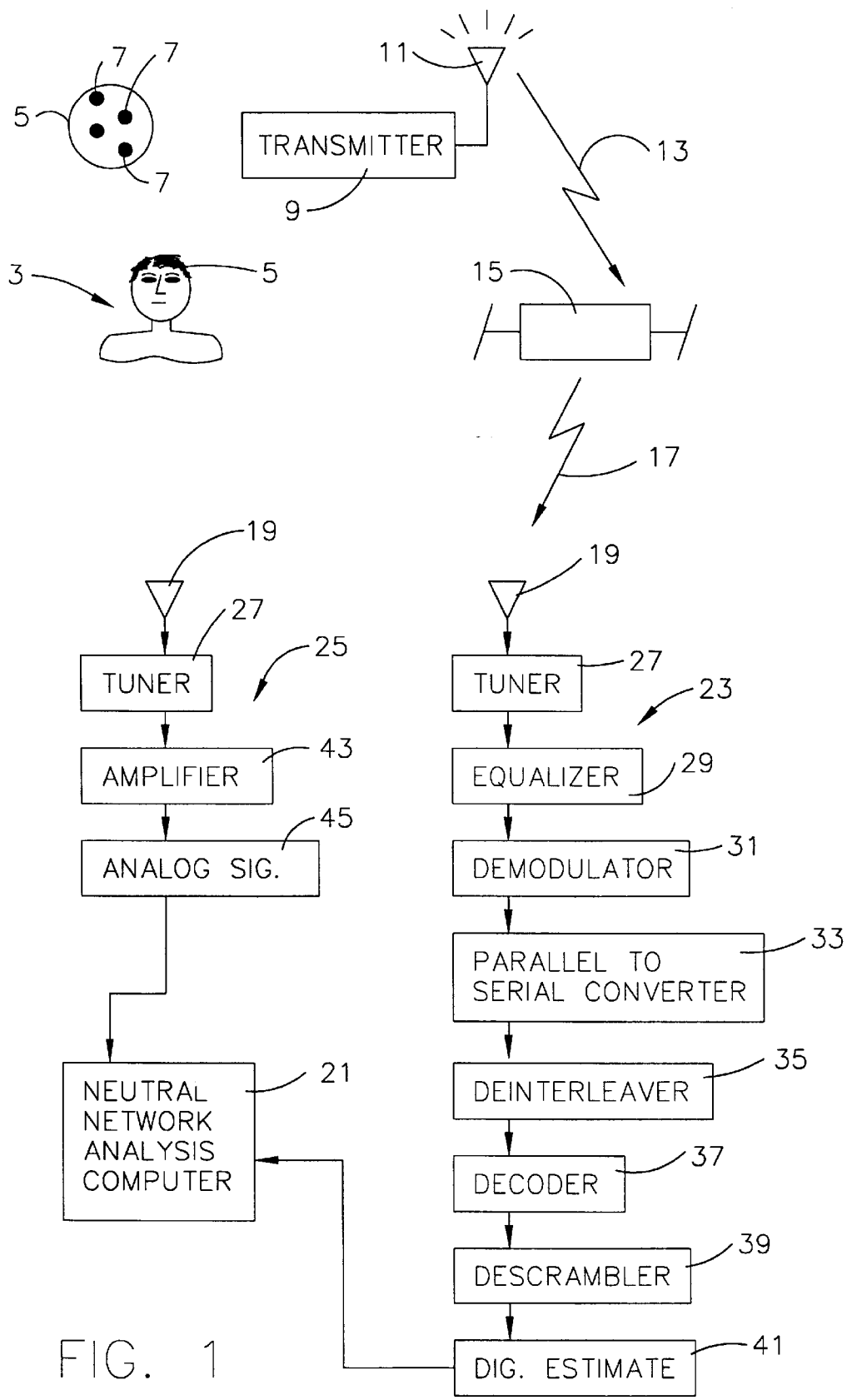
FIG. 1 is a block diagram illustrating the system and method according to a first embodiment of this invention.

FIG. 1 illustrates a particular monitored individual 3 according to an embodiment of this invention. Individual 3 includes a head 5. As illustrated, sensors 7 may be attached or otherwise disposed adjacent to the scalp or skin of the individual 3. Sensors 7 detect and monitor brain activity of individual 3. Sensors 7 can detect event related potentials and/or event related fields (i.e. ERPs or ERFs). Optionally, sensor 7 may be utilized to detect any other type of "brainprint" indicative of brain activity of individual 3.

The monitored "brainprint" of individual 3 is forwarded to a small transmitter 9 which is preferably embedded in the skin of individual 3, or in close proximity to individual 3. Transmitter 9 causes the monitored "brainprint" information detected by sensor 7 to be transmitted by way of antenna 11 as wireless signals 13. In certain embodiments of this invention, signals 13 propagate through atmospheric free space in the form of uplink satellite signals toward satellite 15. Satellite 15 receives signals 13 and then redirects those signals back toward Earth as signals 17 which include information therein (analog or digital) indicative of the monitored brain activity of individual 3. Signals 17 are received by antenna 19. Antenna 19 and individual 3 are both preferably located on Earth at different locations. In certain embodiments, antenna 19 is located at a location remote from individual 3. For example, individual 3, sensor 7, transmitter 9, and antenna 11 may all be located in Europe while receiving antenna 19 and computer 21 may be located in the United States.

FIG. 1 illustrates both a digital embodiment 23 and an analog embodiment 25 of receiving systems. Either may be utilized. When signals 17 include digital information, they are received by antenna 19 and forwarded to tuner 27. The signals are processed through equalizer 29, demodulator 31, parallel to serial converter 33, deinterleaver 35, decoder 37, descrambler 39, digital estimator 41, and finally to neural network analysis or other type of computer 21. Monitored firings of brain nodes may be broken down into digital form (e.g. the firing of a node is equivalent to a "1" and nonfiring to a "0"). These 1s and 0s, which are digital, may be modulated onto a carrier and then transmitted to the satellite so that the monitored brain activity in the signal is in digital form. When the computer receives this monitored signal from the satellite, the demodulating system analyzes the received digital information (e.g. 1s and 0s) which is indicative of the firing of select brain nodes of the monitored individual. These digital signals may be transformed, in certain embodiments, into analog form similar to the illustrations of FIG. 3, or alternatively may be kept in digital form and compared with prestored digital signals to determine what the monitored person was intending to communicate.

In analog embodiments, signal 17 is received by antenna 19, and the information forwarded to tuner 27, amplifier 43, and the analog information inclusive signal 45 is forwarded to computer 21. In analog embodiments, the signals received by the monitoring sensors are in the form of waves similar to those shown in FIG. 3 herein.

Figure 2:
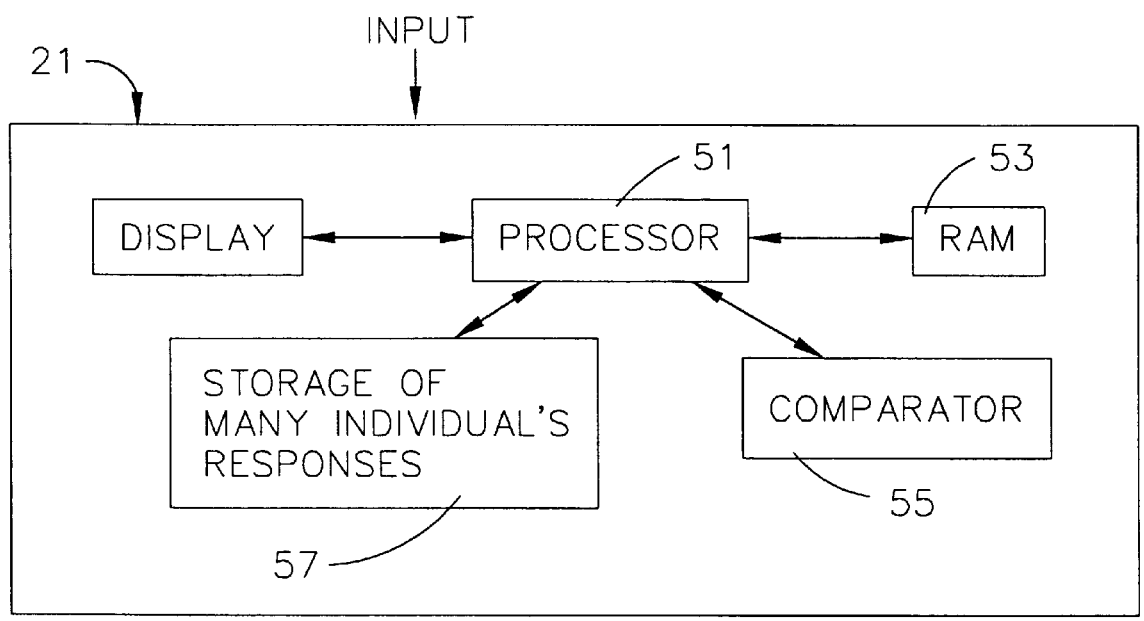
FIG. 2 is a block diagram illustrating the neural network inclusive computer of the FIG. 1 embodiment of this invention.

FIG. 2 is a block diagram of computer 21 in certain embodiments of this invention. The input thereto may be in either analog or digital form. Computer 21 includes processor 51, RAM 53, comparing device 55, and memory 57 for storing a plurality of files or patterns of measured brain activity or responses of particular individuals. For example, memory or storage 57 may include one file for individual X which includes hundreds of monitored brain activity (e.g. ERPs or ERFs) that were measured when individual X was attempting to communicate the word "no." Another file in storage or memory 57 may have stored therein hundreds or thousands of monitored brain patterns or activities of individual X when individual X was attempting to communicate the word "yes." Storage or memory 57 may also include similar files for individual X including patterns which were measured when the individual was attempting to communicate different words or phrases. Each of these files may have a normalized curve, waveform or pattern formed or developed for each word, phrase, or thought for each individual, based upon all of the recorded patterns or curves for that word, phrase, or thought (e.g. 1,000 such recordings for the phrase "help me," and 1,000 for the phrase "I've been caught." Memory 57 further includes in certain embodiments many different files for many different individuals, all including files for each individual's past communicating of particular words, phrases, or thoughts.

Normalized curves or patterns corresponding to each individual's attempt to communicate a particular word, thought, or a pattern may be stored in storage or memory 57. Thus, for individual X attempting to communicate the word "no", a normalized curve, waveform, or a pattern may be stored in memory 57 indicative or such a communication. Likewise, a normalized curve, waveform, or pattern may be stored in memory 57 for individual Y attempting to communicate the word "no" and another distinct normalized curve, waveform, or pattern may be stored in memory 57 for individual Y attempting to communicate the word "yes." In a similar manner, a normalized curve, waveform or pattern may be stored in memory 57 for individual Y attempting to communicate the phrase "I don't know" or "I'm not sure." Thus, if one hundred different human beings have files in memory 57 corresponding to each of these individual's attempt to communicate the phrase "I don't know", then one hundred different normalized waveforms, curves or patterns would be stored in memory 57, each corresponding to a particular individual. A normalized curve, waveform, or pattern may be developed by repeatedly asking an individual tens, hundreds, or thousands of times a particular question or group of questions which evoke a known response such as "I don't know," or "no" or "yes." Each time the response is made, a curve, waveform, or a pattern is recorded. After tens, hundreds, or even thousands of these patterns have been recorded, a normalized curve, waveform or pattern is formed based upon same so as to be indicative of that particular individual's attempt to communicate the phrase. In a similar manner, if it is desired to store normalized curves, waveforms, or patterns for ten different words, phrases or thoughts communicated by a particular individual, then a normalized curve, waveform, or pattern is developed for each of the different ten items so that ten different normalized curves, waveforms or patterns are stored in memory 57 for that individual and classified accordingly. Thus, when computer 21 receives signals indicating brain activity from that monitored individual, the received signals are compared by device 55 to the ten different normalized signals in memory 57 in order to determine what the individual is attempting to communicate.

FIGS. 3(*a*)–3(*f*) illustrate different normalized curves which may be stored in memory 57. FIG. 3(*a*) shows a normalized curve indicative of individual "Joe" attempting to communicate the word "no." FIG. 3(*b*) shows a normalized curve indicative of individual "Joe" attempting to communicate the word "yes." FIG. 3(*c*) shows a normalized curve indicative of another individual "Steve" attempting to communicate the word "no", while FIG. 3(*d*) shows a normalized curve indicative of individual "Steve" attempting to communicate the word "yes." Finally, FIG. 3(*e*) shows a normalized curve indicative of still another individual "Anita" attempting to communicate the word "no", while FIG. 3(*f*) illustrates a normalized curve of "Anita" attempting to communicate the word "yes."

Thus, if computer 21 receives a signal including monitored brain information identified as being from individual "Steve", then computer 21 causes the received signal to be compared by device 55 with the normalized curves or waveforms shown in FIGS. 3(*c*) and 3(*d*) and all others normalized stored signals of "Steve." If a match or a close match is found between the received monitored signal and the normalized curve of FIG. 3(*c*), then the computer determines that "Steve" was attempting to communicate the word "no." Meanwhile, if no match is found with the normalized curve of FIG. 3(*c*), but a match or a substantial match is found with regard to the normalized curve or waveform of FIG. 3(*d*), then the computer determines that "Steve" was attempting to communicate the word "yes." If no match is found between the received "Steve" signal and any normalized curve or waveform of either FIG. 3(*c*) or FIG. 3(*d*), or with any other normalized curve stored in memory 57 corresponding to "Steve", then the computer determines that it is unclear what "Steve" was attempting to communicate.

Thus, different embodiments of this invention may be utilized to help individuals communicate with one another without having to send faxes, make telephone calls, speak, or the like. For instance, military personnel located in the Middle East or Europe can communicate with superiors in the Pentagon, simply by use of monitored brain activity being transmitted by satellite to the Pentagon. Alternatively, a special operations individual (e.g. a spy) located in Europe could be asked a question by way of a telephone call, fax, or the like, and that individual can respond to that question simply by thinking the answer so that that individual's monitored brain activity which is transmitted back to the United States can be analyzed to determine the individual's response. In further embodiments of this invention, twoway human communication is possible, provided that human beings at both locations have equipment capable of analyzing and monitoring received monitored brain activity. In such a manner, individuals at two remote locations may communicate with one another without either individual having to speak a word, write anything down, or the like.

In other embodiments, devices mounted to the person (e.g. underneath the scalp) may be energized in a predetermined manner or sequence to remotely cause particular identified brain node(s) to be fired in order to cause a predetermined feeling or reaction in the individual, such as lack of hunger, lack or depression, lack or thirst, lack of aggression, lack of alzheimer's disease effects, or the like. In an example of such an embodiment, the sensors may be replaced with remote firing devices. The computer may cause satellite signals to be sent to a receiver on or proximate an individual, which receiver forwards instructions to the remote firing devices that are mounted, e.g. under the scalp of the individual, in order to selectively cause same to fire or be energized. Such energizing of the device(s) under or near the scalp in a predetermined manner tend to cause identified brain nodes to fire a predetermined number of times. This is useful, for example, in the following scenarios. For example, the system can be used to identify which brain node(s) in a particular individual are typically fired causing that individual to not be hungry. If that individual has an eating disorder or problems with obesity, then the firing devices can be remotely energized thereby causing the identified brain node(s) to be fired at predetermined or random times in order to cause the individual to not be hungry (even if the individual has not eaten for several hours or several days).

In a similar manner, brain nodes which cause an individual to be jovial or not depressed can be identified, and caused to be remotely fired by the computer and firing devices 7 mounted under the scalp in a predetermined manner or sequence(s) in order to minimize or prevent depression of the individual. This may eliminate the need for drugs such a Prozac. Alternatively, such drug(s) may be administered after such remote node firings, and the nodes at issue thereafter being monitored as discussed above and a biofeedback being performed to determine the effectiveness of the drug(s) or alternatively to enable a system to be utilized combining drug treatment with remote node firings to more effectively prevent or minimize depression of the individual. Thus, the biofeedback may enable the identified nodes to be fired by the firing devices and/or drug treatment at the proper level to most efficiently treat the disease, illness or state. This invention, including remote firings and/or monitoring, is not limited to these examples, and its potential uses are almost endless. Brain node firings can be remotely controlled in a predetermined manner or sequence (s) (even random or sequential) to reduce, minimize, or eliminate undesirable behavior or mental characteristics. This may eliminate or reduce the need for burdensome drug treatments and the like. Brain node firings of a normal person, or of a particular person in a given mental or physical state, may be monitored and the brain activity stored and analyzed in the computer 21 memory. This stored brain activity may then be caused by remotely causing the firing devices to cause particular brain node(s) to be fired at given times or intervals in a predetermined manner or sequence. The computer may be programmed to instruct the brain sensors and/or firing devices to identify which brain nodes are responsible for which types of physical or mental behavior, and then the computer transmits firing instructions to the firing devices for those nodes to cause them to be fired in a predetermined manner to effect such physical or mental behavior.

Once given the above disclosure, many other features, modifications, and improvements will become apparent to the skilled artisan. Such other features, modifications, and improvements are, therefore, considered to be a part of this invention, the scope of which is to be determined by the following claims.

I claim:

1. A method of communicating comprising the steps of:
   providing a first human being at a first location;
   providing a computer at a second location that is remote from the first location;
   providing a satellite;
   providing at least one sensor on the first human being;
   detecting brain activity of the first human being using the at least one sensor, and transmitting the detected brain activity to the satellite as a signal including brain activity information;
   the satellite sending a signal including the brain activity information to the second location;
   a receiver at the second location receiving the signal from the satellite and forwarding the brain activity information in the signal to the computer;
   comparing the received brain activity information of the first human being with normalized or averaged brain activity information relating to the first human being from memory; and
   determining whether the first human being was attempting to communicate particular words, phrases or thoughts, based upon the comparing of the received brain activity information to the information from memory.

2. The method of claim 1, further including the following steps:
   asking the first human being a plurality of questions and recording brain activity of the first human being responsive to the plurality of questions in the process of developing said normalized or averaged brain activity information relating to the first human being stored in the memory.

3. The method of claim 2, wherein the plurality of questions are the same question.

4. The method of claim 2, wherein the plurality of questions are different questions.

5. The method of claim 2, further comprising the step of normalizing or averaging recorded brain activity responsive to a given question or set of questions in developing the normalized or averaged brain activity information relating to the first human being.

6. A method of communicating words from a first location to a second location, the method comprising the steps of:
   providing a first human being at the first location;
   providing a computer at the second location that is remote from the first location;
   providing at least one sensor on the first human being;
   detecting brain activity of the first human being using the at least one sensor wherein the brain activity is indicative of words to be communicated by the first human being, and forwarding the detected brain activity indicative of words to be communicated to the computer at the second location;

comparing the received brain activity of the first human being indicative of words to be communicated with normalized or averaged brain activity information relating to the first human being from memory; and determining words being communicated by the first human being based upon the comparing of the received brain activity information to the information from memory.

7. The method of claim 6, further including asking the first human being a plurality of questions and recording brain activity of the first human being responsive to the plurality of questions in a process of developing the normalized or averaged brain activity information relating to the first human being.

8. The method of claim 6, further comprising the step of the computer outputting words determined in said determining step to a second human being so that words thought or stated by the first human being are communicated by the first human being to the second human being via the computer.

* * * * *